US009630933B2

(12) United States Patent
Miyazaki

(10) Patent No.: US 9,630,933 B2
(45) Date of Patent: Apr. 25, 2017

(54) METHOD FOR PRODUCING 1-H-TETRAZOLE DERIVATIVE

(71) Applicant: Nippon Soda Co., Ltd., Chiyoda-ku, Tokyo (JP)

(72) Inventor: Hidekazu Miyazaki, Takaoka (JP)

(73) Assignee: Nippon Soda Co., Ltd., Tokyo (JP)

( * ) Notice: Subject to any disclaimer, the term of this patent is extended or adjusted under 35 U.S.C. 154(b) by 31 days.

(21) Appl. No.: 14/406,605

(22) PCT Filed: Jun. 7, 2013

(86) PCT No.: PCT/JP2013/065848
§ 371 (c)(1),
(2) Date: Dec. 9, 2014

(87) PCT Pub. No.: WO2013/187327
PCT Pub. Date: Dec. 19, 2013

(65) Prior Publication Data
US 2015/0322021 A1    Nov. 12, 2015

(30) Foreign Application Priority Data

Jun. 12, 2012  (JP) ................................ 2012-132811

(51) Int. Cl.
*C07D 257/04*    (2006.01)
(52) U.S. Cl.
CPC .................... *C07D 257/04* (2013.01)
(58) Field of Classification Search
CPC .................................................. C07D 257/04
See application file for complete search history.

(56) References Cited

U.S. PATENT DOCUMENTS

| 4,526,978 | A | 7/1985 | Klaubert et al. |
| 2005/0070439 | A1 | 3/2005 | Kobori et al. |
| 2012/0004420 | A1 | 1/2012 | Suzumi et al. |

FOREIGN PATENT DOCUMENTS

| DE | 102011014082 A1 | 10/2011 |
| WO | WO 03/016303 A1 | 2/2003 |
| WO | WO 2010/103783 A1 | 9/2010 |
| WO | WO 2011/110651 A1 | 9/2011 |
| WO | WO 2012/024495 A1 | 2/2012 |

OTHER PUBLICATIONS

International Search Report dated Jul. 2, 2013, in PCT/JP2013/065848.
Demko et al., "A Click Chemistry Approach to Tetrazoles by Huisgen 1,3-Dipolar Cycloaddition: Synthesis of 5-Acyltetrazoles from Azides and Acyl Cyanides," Angew. Chem. Int. Ed., 2002, 41(12):2113-2116.
Fuse, Shinichiro, "Organic Synthesis Using Microflow Reactor," Journal of Synthetic Organic Chemistry, Japan, Feb. 2012, 70(2)177-178, with English summary on first page.
Gutmann et al., "Synthesis of 5-Substituted 1H-Tetrazoles from Nitriles and Hydrazoic Acid by Using a Safe and Scalable High-Temperature Microreactor Approach," Angew. Chem. Int. Ed., 2010, 49(39):7101-7105.
Hassner et al. "Utility of a Polymeric Azide Reagent in the Formation of Di- and Triazidomethane. Their NMR Spectra and the X-ray Structure of Derived Triazoles," J. Org. Chem., 1990, 55:2304-2306.
Palde et al., "Safe and Efficient Tetrazole Synthesis in a Continuous-Flow Microreactor," Angew. Chem. Int. Ed., 2011, 50:3525-3528.
Supplementary European Search Report dated Oct. 2, 2015, in EP 13805023.2.

*Primary Examiner* — Rebecca Anderson
*Assistant Examiner* — Karen Cheng
(74) *Attorney, Agent, or Firm* — Foley & Lardner LLP

(57) ABSTRACT

The present invention provides a method for producing a 1H-tetrazole derivative by reacting an azide compound represented by general formula (II) and a cyanide compound represented by general formula (III) in a flow reactor to produce a compound represented by general formula (I) (wherein, Y represents an alkyl group, aryl group, arylalkyl group, substituted silyl group or substituted silylalkyl group, Z represents —CO—, —SO$_2$— or —CR$_a$R$_b$— (wherein, R$_a$ and R$_b$ respectively and independently represent a hydrogen atom, alkyl group or unsubstituted or substituted aryl group), p represents 0 or 1, q represents 0 or 1, r represents 0 or 1 (provided that q is 1 in the case p is 0 or r is 0), R$^1$ represents an alkyl group or hydrogen atom in the case q is 0 or an alkylene group in the case q is 1, and R$^2$ represents an unsubstituted or substituted aryl group).

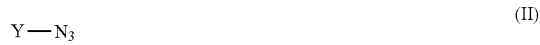
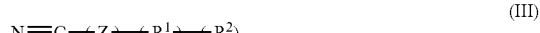
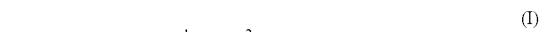

4 Claims, No Drawings

METHOD FOR PRODUCING 1-H-TETRAZOLE DERIVATIVE

CROSS-REFERENCE TO RELATED APPLICATIONS

This application is a National Stage application of PCT/JP2013/065848, filed Jun. 7, 2013, which claims priority from Japanese application JP 2012-132811, filed Jun. 12, 2012.

TECHNICAL FIELD

The present invention relates to a method for producing a 1H-tetrazole derivative. More particularly, the present invention relates to a method for reacting an azide compound with a cyanide compound in a flow reactor.

The present application claims priority on the basis of Japanese Patent Application No. 2012-132811 filed in Japan on Jun. 12, 2012, the contents of which are incorporated herein by reference.

BACKGROUND ART

Numerous chemicals have been proposed for controlling diseases of agricultural and horticultural crops. For example, Patent Document 1 discloses a tetrazoyl oxime derivative having superior pharmacological efficacy on useful plants and proposes the use thereof as a plant disease control agent. Examples of methods for producing the tetrazoyl oxime derivative disclosed in Patent Document 1 include the method described in Patent Document 2 whereby a hydroxylamine is reacted with a 1-alkyl-5-benzoyl-1H-tetrazole derivative represented by the following general formula (P) and the resulting tetrazoylhydroxyimino derivative is used as raw material to produce a tetrazoyl oxime derivative.

[Chemical Formula 1]

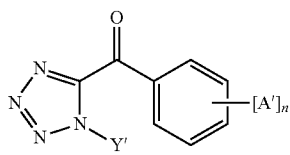

(P)

In general formula (P), A' represents a halogen atom, alkyl group, alkoxy group, methanesulfonyl group, trifluoromethyl group, aryl group, cyano group or nitro group, n represents an integer of 0 to 5, and Y' represents an optionally substituted alkyl group.

The method for producing the 1-alkyl-5-benzoyl-1H-tetrazole derivative represented by general formula (P) preferably consists of directly reacting benzoyl cyanide and an alkyl azide followed by forming a tetrazole ring by a cycloaddition reaction since it is easy to control the locations of substituents on the tetrazole ring.

For example, Non-Patent Document 1 reports that (1-benzyl-1H-tetrazol-5-yl)(phenyl)methanone was able to be synthesized by reacting benzoyl cyanide and benzyl azide for 60 hours in an autoclave. However, although the aforementioned method does not present problems in the case the alkyl azide used as raw material has a group having a comparatively long carbon chain such as a benzyl group, in the case of using a highly explosive raw material having a low boiling point in the manner of methyl azide, it becomes extremely difficult to carry out the method from the viewpoint of safety. Moreover, there is also the problem of the reaction requiring a long period of time to obtain an adequate reaction yield.

In addition, Patent Document 3 reports that 1-methyl-5-tosyl-1H-tetrazole was able to be synthesized by reacting methyl azide and tosyl cyanide in an explosion-proof, sealed autoclave. However, since highly reactive tosyl cyanide is used as a raw material in the aforementioned method, the target reaction product is obtained under comparatively low temperature conditions of 80° C., and reaction efficiency becomes extremely low in the case of using a benzoyl cyanide having a lower level of reactivity.

Moreover, Patent Document 4 reports that a compound represented by general formula (P') (wherein, A' and n are the same as in general formula (P)) was able to be synthesized efficiently and safely by reacting an alkyl isocyanide such as methyl isocyanide with an acid halide such as benzoyl chloride followed by reacting the aforementioned reaction product with sodium azide. However, the method described in the aforementioned document requires that the methyl isocyanide be isolated due to concerns over explosion and toxicity. Moreover, it is extremely difficult to industrialize the aforementioned method due to the extremely distressing odor of methyl isocyanide.

[Chemical Formula 2]

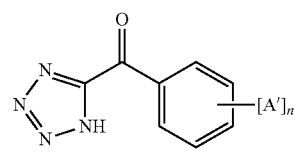

(P')

In addition, Non-Patent Document 2 reports that a tetrazole cyclization reaction was carried out by reacting benzyl cyanide and sodium azide in a flow reactor. However, a reaction using benzoyl cyanide and methyl azide as raw materials is not disclosed.

PRIOR ART DOCUMENTS

Patent Documents

Patent Document 1: International Publication No. WO 2003/016303

Patent Document 2: International Publication No. WO 2010/103783

Patent Document 3: U.S. Pat. No. 4,526,978 Patent Document 4: International Publication No. WO 2011/110651

Non-Patent Documents

Non-Patent Document 1: Zachary, et al., Angewandte Chemie International Edition, 2002, Vol. 41(12), p. 2113-2116

Non-Patent Document 2: Gutmann, et al., Angewandte Chemie International Edition, 2010, Vol. 49(39), p. 7101-7105

DISCLOSURE OF THE INVENTION

Problems to be Solved by the Invention

An object of the present invention is to provide a method for efficiently and safely producing a 1H-tetrazole derivative using an azide compound and cyanide compound as raw materials.

Means for Solving the Problems

As a result of conducting extensive studies to solve the aforementioned problems, the inventors of the present invention found that a 1H-tetrazole derivative having substituents at the 1-position and 5-position can be produced industrially safely and efficiently by reacting an azide compound and a cyanide compound using a flow reactor for the reaction vessel, thereby leading to completion of the present invention.

Namely, the method for producing a 1H-tetrazole derivative of the present invention includes the aspects described in [1] to [6] below.

[1] A method for producing a 1H-tetrazole derivative, comprising: reacting an azide compound represented by the following general formula (II) (wherein, Y represents an alkyl group, aryl group, arylalkyl group, substituted silyl group or substituted silylalkyl group) with a cyanide compound represented by the following general formula (III) (wherein, Z represents —CO—, —SO$_2$— or —CR$_a$R$_b$— (wherein, R$_a$ and R$_b$ respectively and independently represent a hydrogen atom, alkyl group or unsubstituted or substituted aryl group), p represents 0 or 1, q represents 0 or 1, r represents 0 or 1, R$^1$ represents an alkyl group or hydrogen atom in the case q is 0 or an alkylene group or hydrogen atom in the case q is 1 and R$^2$ represents an unsubstituted or substituted aryl group, provided that q is 1 in the case p is 0 and q is 1 in the case r is 0) in a flow reactor to produce a compound represented by the following general formula (I) (wherein, Y is the same as defined in general formula (II) and Z, R$^1$, R$^2$, p, q and r are the same as defined in general formula (III)).

[Chemical Formula 3]

(II)

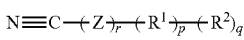
(III)

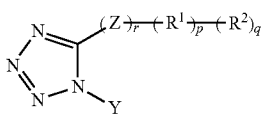
(I)

[2] The method for producing a 1H-tetrazole derivative of [1] above, wherein Y represents an alkyl group.

[3] The method for producing a 1H-tetrazole derivative of [1] or [2] above, wherein R$^2$ is a group represented by the following general formula (s1) (wherein, A represents a halogen atom, alkyl group, haloalkyl group, alkoxy group, haloalkoxy group, alkylsulfonyl group, unsubstituted or substituted aryl group, cyano group or nitro group, n represents an integer of 0 to 5, A may be mutually the same or different when n is 2 or more, and the asterisk (*) represents bonding to R$^1$ in the case p is 1 in the general formula (III), bonding to Z in the case p is 0 and r is 1 or binding to a carbon atom of a cyanido group in the case p and r are 0).

[Chemical Formula 4]

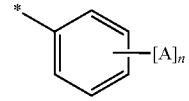
(s1)

[4] The method for producing a 1H-tetrazole derivative of any of [1] to [3] above, wherein the reaction temperature of the reaction is 150° C. to 250° C.

[5] The method for producing a 1H-tetrazole derivative of any of [1] to [4] above, wherein the reaction solution of the reaction contains the azide compound represented by general formula (II) in an amount equal to 1.4 times or more the number of moles of the cyanide compound represented by general formula (III).

[6] The method for producing a 1H-tetrazole derivative of any of [1] to [5] above, wherein the solvent in the reaction solution of the reaction is toluene or N-methylpyrrolidone.

Effects of the Invention

The method for producing a 1H-tetrazole derivative of the present invention enables the production of a 1H-tetrazole derivative, which has substituents at the 1-position and 5-position and is useful as a synthesis raw material of active ingredients of agricultural chemicals and various other types of chemicals, in one step by using an azide compound and a cyanide compound as raw materials. In particular, since the reaction is carried out in a flow reactor, the 1H-tetrazole derivative can be produced industrially safely, in a short period of time and with high efficiency despite using a highly explosive azide compound.

BEST MODE FOR CARRYING OUT THE INVENTION

Although the following provides an explanation of preferable examples of the present invention, the present invention is not limited to these examples. Constituents of the present invention (to also be referred to as "the production method of the present invention") can be added, omitted, substituted or altered in other ways within a range that does not deviate from the gist of the present invention.

The method for producing a 1H-tetrazole derivative of the present invention is a method for producing a 1H-tetrazole derivative represented by the following general formula (I) by reacting an azide compound and a cyanide compound in a flow reactor.

[Chemical Formula 5]

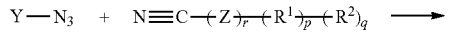

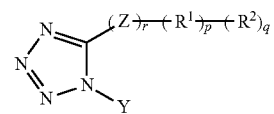
(I)

(In general formulas (II) and (I), Y represents an alkyl group, aryl group, arylalkyl group, substituted silyl group or substituted silylalkyl group. In general formula (III) and (I), Z represents —CO—, —SO$_2$— or —CR$_a$R$_b$— (wherein, R$_a$ and R$_b$ respectively and independently represent a hydrogen atom, alkyl group or unsubstituted or substituted aryl group), p represents 0 or 1, q represents 0 or 1, r represents 0 or 1, R$^1$ represents an alkyl group or hydrogen atom in the case q is 0 or an alkylene group in the case q is 1 and R$^2$ represents an unsubstituted or substituted aryl group, provided that q is 1 in the case p is 0 and q is 1 in the case r is 0.)

In the production method of the present invention, the azido group of the azide compound represented by general formula (II) is cycloadded to the cyanido group of the cyanide compound represented by general formula (III). As a result, in comparison with a synthesis method in which a substituent is introduced into a compound having a tetrazole backbone, a 1H-tetrazole derivative having substituents introduced at the 1-position and 5-position can be produced both selectively and efficiently. In addition, by reacting the azide compound and cyanide compound in a flow reactor, the target 1H-tetrazole derivative can be produced safely and in a short period of time even in the case of using a highly explosive azide compound as a raw material.

[Azide Compound Represented by General Formula (II)]

In general formula (II), Y represents an alkyl group, unsubstituted or substituted aryl group, unsubstituted or substituted arylalkyl group, substituted silyl group or substituted silylalkyl group.

[Chemical Formula 6]

Y—N$_3$          (II)

The alkyl group may be a linear alkyl group, branched alkyl group or cyclic alkyl group. The aforementioned alkyl group is preferably a linear alkyl group having 1 to 8 carbon atoms, a branched alkyl group having 3 to 8 carbon atoms or a cyclic alkyl group having 3 to 8 carbon atoms. Specific examples include a methyl group, ethyl group, n-propyl group, i-propyl group, n-butyl group, i-butyl group, s-butyl group, t-butyl group, n-pentyl group, n-hexyl group, cyclopropyl group, cyclobutyl group, cyclopentyl group and cyclohexyl group.

The unsubstituted or substituted aryl group may be a monocyclic group or polycyclic group. In the case of a polycyclic aryl group, as long as at least one of the rings is an aromatic ring, the remaining rings may be saturated rings, unsaturated rings or aromatic rings. In the case Y in general formula (II) is a substituted aryl group, there are no particular limitations on the substituent provided it is a chemically acceptable substituent, and specific examples thereof include the substituents listed in (1) to (85) to be subsequently described. An aryl group having 6 to 10 carbon atoms is preferable for the aryl group represented by Y in general formula (II), a phenyl group, 1-napthyl group, 2-naphthyl group, azulenyl group, indanyl group or tetralinyl group is more preferable, and a phenyl group is even more preferable.

An unsubstituted or substituted arylalkyl group refers to a group in which at least one hydrogen atom of the alkyl group is substituted with an unsubstituted or substituted aryl group. The alkyl group substituted with an aryl group may be a linear alkyl group, branched alkyl group or cyclic alkyl group. The aforementioned alkyl group is preferably a linear alkyl group having 1 to 8 carbon atoms, a branched alkyl group having 3 to 8 carbon atoms or a cyclic alkyl group having 3 to 8 carbon atoms, and is more preferably a linear alkyl group having 1 to 8 carbon atoms. In addition, examples of aryl groups serving as a substituent of the alkyl group are the same as the examples of the aforementioned unsubstituted or substituted aryl group. Y in general formula (II) preferably represents a group in which one hydrogen atom of a linear alkyl group having 1 to 8 carbon atoms is substituted with an unsubstituted or substituted aryl group having 1 to 6 carbon atoms, more preferably represents a group in which one hydrogen atom of a linear alkyl group having 1 to 8 carbon atoms is substituted with an unsubstituted or substituted phenyl group, even more preferably represents a group in which one hydrogen atom of a linear alkyl group having 1 to 8 carbon atoms is substituted with an unsubstituted phenyl group, and still more preferably represents a benzyl group.

A substituted silyl group is a group in which at least one hydrogen atom of the silyl group is substituted. There are no particular limitations on the substituent provided it is a chemically acceptable substituent. Specific examples thereof include the substituents listed in (1) to (85) to be subsequently described. In addition, in the case 2 or 3 hydrogen atoms are substituted, the substituents may be mutually the same or different. Y in general formula (II) preferably represents a silyl group in which 1 to 3 hydrogen atoms are substituted by the same or different alkyl groups, more preferably represents a silyl group in which three hydrogen atoms are substituted with the same or different alkyl groups, even more preferably represents a trimethylsilyl group, triethylsilyl group, ethyldimethylsilyl group or t-butyldimethylsilyl group, and still more preferably represents a trimethylsilyl group.

A substituted silylalkyl group is a group in which at least one hydrogen atom of the alkyl group is substituted with a substituted silyl group. The alkyl group substituted with the silyl group may be a linear alkyl group, branched alkyl group or cyclic alkyl group. The aforementioned alkyl group is preferably a linear alkyl group having 1 to 8 carbon atoms, a branched alkyl group having 3 to 8 carbon atoms or a cyclic alkyl group having 3 to 8 carbon atoms, and is more preferably a linear alkyl group having 1 to 8 carbon atoms. In addition, examples of silyl groups serving as a substituent of the alkyl group are the same as the examples of the aforementioned substituted silyl group. Y in general formula (II) preferably represents a group in which one hydrogen atom of a linear alkyl group having 1 to 8 carbon atoms is substituted with a substituted silyl group, more preferably represents a group in which one hydrogen atom of a linear alkyl group having 1 to 8 carbon atoms is substituted with a silyl group in which one to three hydrogen atoms are substituted with the same or different alkyl groups, even more preferably represents a group in which one hydrogen atom of a linear alkyl group having 1 to 3 carbon atoms is substituted with a trimethylsilyl group, triethylsilyl group, ethyldimethylsilyl group or t-butyldimethylsilyl group, and still more preferably represents a trimethylsilylmethyl group.

The azide compound represented by general formula (II) is preferably that in which Y represents a linear alkyl group having 1 to 8 carbon atoms, a branched alkyl group having 3 to 8 carbon atoms, a cyclic alkyl group having 3 to 8 carbon atoms, an unsubstituted or substituted phenyl group or an unsubstituted or substituted benzyl group, and more preferably that in which Y represents a linear alkyl group having 1 to 6 carbon atoms, a branched alkyl group having 3 to 6 carbon atoms or a cyclic alkyl group having 3 to 6 carbon atoms. In the production method of the present invention, since the reaction is carried out in a flow reactor, a 1H-tetrazole derivative can be produced safely and efficiently even in the case of using as a raw material a lower alkyl azide having 6 carbon atoms or less that is generally considered to be explosive and toxic due to the low boiling point thereof. In particular, the azide compound represented by general formula (II) is even more preferably that in which Y represents a linear alkyl group having 1 to 3 carbon atoms and particularly preferably methyl azide.

The azide compound represented by general formula (II) can be synthesized from a known compound using a known chemical reaction. For example, among azide compounds represented by general formula (II), methyl azide can be synthesized by dropping dimethyl sulfate into sodium azide and allowing to react in the presence of base at 80° C. (refer to, for example, Journal of Organic Chemistry, 1990, Vol. 55, pp. 2304-2306).

[Cyanide Compound Represented by General Formula (III)]

In general formula (III), Z represents —CO—, —$SO_2$— or —$CR_aR_b$—, p represents 0 or 1, q represents 0 or 1, r represents 0 or 1, $R^1$ represents an alkyl group or hydrogen atom in the case q is 0 or an alkylene group in the case q is 1 and $R^2$ represents an unsubstituted or substituted aryl group, provided that q is 1 in the case p is 0 and q is 1 in the case r is 0. $R_a$ and $R_b$ respectively and independently represent a hydrogen atom, alkyl group or unsubstituted or substituted aryl group.

[Chemical Formula 7]

N≡C—(—Z—)$_r$—(—$R^1$—)$_p$—(—$R^2$)$_q$ (III)

In general formula (III), Z represents —CO— (carbonyl group), —$SO_2$— (sulfonyl group) or —$CR_aR_b$— (wherein, $R_a$ and $R_b$ respectively and independently represent a hydrogen atom, alkyl group or unsubstituted or substituted aryl group), and r represents 0 or 1. However, q is always 1 in the case r is 0. In the case $R_a$ or $R_b$ in Z is an alkyl group, examples of the aforementioned alkyl group are the same as the alkyl groups listed as examples of Y in the aforementioned general formula (II). In addition, in the case $R_a$ or $R_b$ in Z is an unsubstituted or substituted aryl group, examples of the aforementioned aryl group are the same as the unsubstituted or substituted aryl groups listed as examples of Y in the aforementioned general formula (II).

In the case Z in general formula (III) represents —$CR_aR_b$—, specific examples thereof include a methylene group (—$CH_2$—) in which both $R_a$ and $R_b$ are hydrogen atoms, a group in which either one of $R_a$ and $R_b$ is a hydrogen atom while the other is an alkyl group, a group in which either one of $R_a$ and $R_b$ is a hydrogen atom and the other is an unsubstituted or substituted aryl group, and a group in which $R_a$ and $R_b$ mutually and independently represent an alkyl group or unsubstituted or substituted aryl group.

Specific examples of Z in general formula (III) include the divalent groups indicated below.

[Chemical Formula 8]

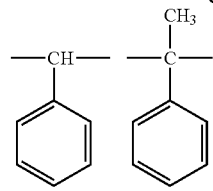

Z in general formula (III) is more preferably —CO— or —$SO_2$— than —$CR_aR_b$—. In comparison with an alkyl nitrile or benzyl cyanide derivative in which a cyano group is bound directly to an alkyl group or alkylaryl group, the use of a cyanide derivative in which a cyano group is bound to an alkyl group and the like through a carbonyl group or sulfonyl group allows the reaction to proceed more efficiently.

In addition, a cyanide derivative in which the group adjacent to the cyano group is a carbonyl group tends to result in lower reactivity than a cyanide derivative in which the group adjacent to the cyano group is a sulfonyl group. In the production method of the present invention, since the reaction is carried out in a flow reactor, even in the case of using as a raw material a cyanide derivative in which the group adjacent to the cyano group is a carbonyl group, a 1H-tetrazole derivative can be produced with sufficiently high reaction efficiency and in a short period of time.

In the case q is 0 in general formula (III), $R^1$ represents an alkyl group or hydrogen atom. Examples of the aforementioned alkyl group are the same as the alkyl groups listed as examples of Y in the aforementioned general formula (II). $R^1$ in general formula (III) preferably represents a linear alkyl group having 1 to 8 carbon atoms, a branched alkyl group having 3 to 8 carbon atoms or a cyclic alkyl group having 3 to 8 carbon atoms.

In the case q is 1 in general formula (III), $R^1$ represents an alkylene group. The aforementioned alkylene group may be a linear alkylene group, branched alkylene group or cyclic alkylene group. The aforementioned alkylene group is preferably a linear alkylene group having 1 to 8 carbon atoms, a branched alkylene group having 3 to 8 carbon atoms or a cyclic alkylene group having 3 to 8 carbon atoms, and is more preferably a linear alkylene group having 1 to 6 carbon atoms, a branched alkylene group having 3 to 6 carbon atoms or a cyclic alkylene group having 3 to 6 carbon atoms. Specific examples include a methylene group, ethylene group, n-propylene group, i-propylene group, n-butylene group, i-butylene group, n-pentylene group, n-hexylene group, cyclopropylene group, cyclobutylene group, cyclopentylene group and cyclohexylene group. Among these, $R^1$ in general formula (III) in the case q is 1 preferably represents a linear alkylene group having 1 to 3 carbon atoms or a branched alkylene group having 3 carbon atoms, more preferably represents a linear alkylene group having 1 to 3 carbon atoms, and even more preferably represents a methylene group.

The cyanide compound represented by general formula (III) is preferably [—($R^1$)p-($R^2$) q] from the viewpoint that reaction yield is enhanced as a result of being a group that has highly electron attracting characteristics. Consequently, among compounds represented by general formula (III), in the case of compounds in which r is 0 and compounds in which r is 1, compounds in which p is 0 or 1 and q is 1 are preferable to compounds in which p is 1 and q is 0, while compounds in which p is 0 and q is 1 are more preferable.

In general formula (III), $R^2$ represents an unsubstituted or substituted aryl group and q represents 0 or 1. However, q is 1 in the case p is 0. The aforementioned aryl group may be a monocyclic group or polycyclic group. Furthermore, as long as at least one ring of a polycyclic aryl group is an aromatic ring, the remaining rings may be saturated rings, unsaturated rings or aromatic rings. In the case $R^2$ in general formula (III) is a substituted aryl group, there are no particular limitations on the aforementioned substituent provided it is a chemically acceptable substituent, and specific examples thereof include the substituents listed in (1) to (85) to be subsequently described.

$R^2$ in general formula (III) preferably represents an aryl group having 6 to 10 carbon atoms and more preferably represents a phenyl group. More specifically, $R^2$ is particularly preferably a group represented by the following general formula (s1).

[Chemical Formula 9]

(s1)

(In general formula (s1), A represents a halogen atom, alkyl group, haloalkyl group, alkoxy group, haloalkoxy group, alkylsulfonyl group, unsubstituted or substituted aryl group, cyano group or nitro group, n represents an integer of 0 to 5, A may be mutually the same or different when n is 2 or more, and the asterisk (*) represents bonding to $R^1$ in the case p is 1 in the general formula (III), bonding to Z in the case p is 0 and r is 1 or binding to a carbon atom of a cyanido group in the case p and r are 0).

In general formula (s1), n is an integer of 0 to 5, preferably an integer of 0 to 3 and more preferably 0. Furthermore, A may be mutually the same or different when n is 2 or more.

In general formula (s1), A represents a halogen atom, alkyl group, haloalkyl group, alkoxy group, haloalkoxy group, alkylsulfonyl group, unsubstituted or substituted aryl group, cyano group or nitro group.

Examples of halogen atoms include a fluorine atom, chlorine atom, bromine atom and iodine atom.

Examples of alkyl groups include a methyl group, ethyl group, n-propyl group, i-propyl group, n-butyl group, i-butyl group, s-butyl group, t-butyl group, n-pentyl group and n-hexyl group. The number of carbon atoms that compose the alkyl group is preferably 1 to 8.

Examples of haloalkyl groups include a fluoromethyl group, chloromethyl group, bromomethyl group, difluoromethyl group, dichloromethyl group, trifluoromethyl group, trichloromethyl group, trifluoroethyl group, pentafluoroethyl group, 3,3,3,2,2-pentafluoropropyl group and 2,2,2-trifluoro-1-trifluoromethylethyl group. The number of carbon atoms that compose the haloalkyl group is preferably 1 to 8.

Examples of alkoxy groups include a methoxy group, ethoxy group, n-propoxy group, i-propoxy group, n-butoxy group, i-butoxy group, s-butoxy group, t-butoxy group and n-hexyloxy group. The number of carbon atoms that compose the alkoxy group is preferably 1 to 8.

Examples of haloalkoxy groups include a 2-chloro-n-propoxy group, 2,3-dichlorobutoxy group and trifluoromethoxy group. The number of carbon atoms that compose the haloalkoxy group is preferably 1 to 8.

Examples of alkylsulfonyl groups include a methylsulfonyl group, ethylsulfonyl group, n-propylsulfonyl group, i-propylsulfonyl group and t-butylsulfonyl group. The number of carbon atoms that compose the alkylsulfonyl group is preferably 1 to 8.

An aryl group refers to a monocyclic or polycyclic aryl group. Furthermore, as long as at least one ring of a polycyclic aryl group is an aromatic ring, the remaining rings may be saturated rings, unsaturated rings or aromatic rings. Among aryl groups, aryl groups having 6 to 10 carbon atoms are preferable.

Specific examples of unsubstituted aryl groups include a phenyl group, 1-napthyl group, 2-naphthyl group, azulenyl group, indanyl group and tetralinyl group.

There are no particular limitations on "substituents" in a substituted aryl group provided they are chemically acceptable substituents. Specific examples thereof include the following substituents:

(1) halogen atoms such as a fluorine atom, chlorine atom, bromine atom or iodine atom; (2) alkyl groups such as a methyl group, ethyl group, n-propyl group, i-propyl group, n-butyl group, s-butyl group, i-butyl group, t-butyl group, n-pentyl group or n-hexyl group; (3) cycloalkyl groups such as a cyclopropyl group, cyclobutyl group, cyclopentyl group, cyclohexyl group or cycloheptyl group; (4) alkoxy groups such as a methoxy group, ethoxy group, n-propoxy group, i-propoxy group, n-butoxy group, i-butoxy group, s-butoxy group or t-butoxy group; (5) alkenyl groups such as a vinyl group, 1-propenyl group, 2-propenyl group, 1-butenyl group, 2-butenyl group, 3-butenyl group, 1-methyl-2-propenyl group, 2-methyl-2-propenyl group, 1-pentenyl group, 2-pentenyl group, 3-pentenyl group, 4-pentenyl group, 1-methyl-2-butenyl group, 2-methyl-2-butenyl group, 1-hexenyl group, 2-hexenyl group, 3-hexenyl group, 4-hexenyl group or 5-hexenyl group;

(6) cycloalkenyl groups such as a 2-cyclopropenyl group, 2-cyclopentenyl group, 3-cyclohexenyl group or 4-cyclooctenyl group; (7) alkenyloxy groups such as a vinyloxy group, allyloxy group, 1-propenyloxy group or 2-butenyloxy group; (8) alkynyl groups such as an ethynyl group, 1-propynyl group, 2-propynyl group, 1-butynyl group, 2-butynyl group, 3-butynyl group, 1-methyl-2-propynyl group, 2-methyl-3-butynyl group, 1-pentynyl group, 2-pentynyl group, 3-pentynyl group, 4-pentynyl group, 1-methyl-2-butynyl group, 2-methyl-3-pentynyl group, 1-hexynyl group or 1,1-dimethyl-2-butynyl group; (9) alkynyloxy groups such as an ethynyloxy group or propargyloxy group; (10) aryl groups such as a phenyl group, 1-naphthyl group or 2-naphthyl group;

(11) aryloxy groups such as a phenoxy group or 1-naphthoxy group; (12) aralkyl groups such as a benzyl group or phenethyl group; (13) aralkyloxy groups such as a benzyloxy group or phenethyloxy group; (14) acyl groups such as a formyl group, acetyl group, propionyl group, benzoyl group, cyclohexylcarbonyl group or phthaloyl group; (15) alkoxycarbonyl groups such as a methoxycarbonyl group, ethoxycarbonyl group, n-propoxycarbonyl group, i-propoxycarbonyl group, n-butoxycarbonyl group or t-butoxycarbonyl group; (16) carboxyl groups; (17) hydroxyl groups; (18) haloalkyl groups such as a chloromethyl group, chloroethyl group, 1,2-dichloro-n-propyl group, 1-fluoro-n-butyl group or perfluoro-n-pentyl group; (19) haloalkoxy groups such as a 2-chloro-n-propoxy group, 2,3-dichlorobutoxy group or trifluoromethoxy group; (20) haloalkenyl groups such as a 2-chloro-1-propenyl group or 2-fluorolbutenyl group; (21) haloalkynyl groups such as a 4,4-dichloro-1-butynyl group, 4-fluoro-1-pentynyl group or 5-bromo-2-pentynyl group;

(22) haloalkenyloxy groups such as a 2-chloro-1-propenyloxy group or 3-bromo-2-butenyloxy group; (23) haloalkynyl groups such as a 3-chloropropargyl group or 3-iodopropargyl group; (24) haloalkynyloxy groups such as a 3-chloropropargyloxy group or 3-iodopropargyloxy group; (25) haloaryl groups such as a 4-chlorophenyl group, 4-fluorophenyl group or 2,4-dichlorophenyl group; (26) haloaryloxy groups such as a 4-fluorophenoxy group or 4-chloro-1-naphthoxy group; (27) halogen-substituted acyl groups such as a chloroacetyl group, trifluoroacetyl group, trichloroacetyl group or 4-chlorobenzoyl group; (28) alkoxyalkyl groups such as a methoxymethyl group, ethoxymethyl group, 1-ethoxyethyl group or 2-ethoxyethyl group; (29) alkoxyalkoxy groups such as a methoxymethoxy group, ethoxymethoxy group, 1-ethoxyethoxy group or 2-ethoxyethoxy group; (30) cyano groups;

(31) isocyano groups; (32) nitro groups; (33) isocyanato groups; (34) cyanato groups; (35) amino groups ($NH_2$ groups); (36) alkylamino groups such as a methylamino group, dimethylamino group or diethylamino group; (37) arylamino groups such as an anilino group, naphthylamino group or anthranylamino group; (38) aralkylamino groups such as a benzylamino group or phenethylamino group; (39) alkylsulfonylamino groups such as a methylsulfonylamino group, ethylsulfonylamino group, n-propylsulfonylamino group, i-propylsulfonylamino group or n-butylsulfonylamino group; (40) arylsulfonylamino groups such as a phenylsulfonylamino group;

(41) heteroarylsulfonylamino groups such as a pyrazinylsulfonylamino group; (42) acylamino groups such as a formylamino group, acetylamino group, propanoylamino group, butyrylamino group, i-propylcarbonylamino group or benzoylamino group; (43) alkoxycarbonylamino groups such as a methoxycarbonylamino group or ethoxycarbonylamino group; (44) haloalkylsulfonylamino groups such as a fluoromethylsulfonylamino group, chloromethylsulfonylamino group, bromomethylsulfonylamino group, difluoromethylsulfonylamino group, dichloromethylsulfonylamino group, 1,1-difluoroethylsulfonylamino group, trifluoromethylsulfonylamino group, 2,2,2-trifluoroethylsulfonylamino group or pentafluoroethylsulfonylamino group; (45) bis(alkylsulfonyl)amino groups such as bis(methylsulfonyl)amino group, bis(ethylsulfonyl)amino group, (ethylsulfonyl)(methylsulfonyl)amino group, bis(n-propylsulfonyl)amino group, bis(i-propylsulfonyl) amino group, bis(n-butylsulfonyl)amino group or bis(t-butylsulfonyl)amino group;

(46) bis(haloalkylsulfonyl)amino groups such as a bis(fluoromethylsulfonyl)amino group, bis(chloromethylsulfonyl)amino group, bis(bromomethylsulfonyl)amino group, bis(dichloromethylsulfonyl)amino group, bis(1,1-difluoroethylsulfonyl)amino group, bis(trifluoromethylsulfonyl)amino group, bis(2,2,2-trifluoroethylsulfonyl)amino group or bis(pentafluoroethylsulfonyl)amino group; (47) unsubstituted or substituted hydrazino groups such as a hydrazino group, N'-phenylhydrazino group, N'-methoxycarbonylhydrazino group, N'-acetylhydrazino group or N'-methylhydrazino group; (48) unsubstituted or substituted aminocarbonyl groups such as a aminocarbonyl group, dimethylaminocarbonyl group, phenylaminocarbonyl group or N-phenyl-N-methyaminocarbonyl group; (49) unsubstituted or substituted hydrazinocarbonyl groups such as a hydrazinocarbonyl group, N'-methylhydrazinocarbonyl group or N'-phenylhydrazinocarbonyl group; (50) unsubstituted or substituted iminoalkyl groups such as a N-methyliminomethyl group, 1-N-phenyliminoethyl group, N-hydroxyiminomethyl group or N-methoxyiminomethyl group;

(51) thiol groups; (52) isothiocyanato groups; (53) thiocyanato groups; (54) alkylthio groups such as a methylthio group, ethylthio group, n-propylthio group, i-propylthio group, n-butylthio group, i-butylthio group, s-butylthio group or t-butylthio group; (55) alkenylthio groups such as a vinylthio group or allylthio group; (56) alkynylthio groups such as a ethynylthio group or propargylthio group; (57) arylthio groups such as a phenylthio group or napthylthio group; (58) heteroarylthio groups such as a 2-pyridylthio group or 3-pyridazylthio group; (59) aralkylthio groups such as a benzylthio group or phenethylthio group; (60) heteroarylalkylthio groups such as a 2-pyridylmethylthio group or 2-furylmethylthio group; (61) alkylthiocarbonyl groups such as a methylthiocarbonyl group, ethylthiocarbonyl group, n-propylthiocarbonyl group, i-propylthiocarbonyl group, n-butylthiocarbonyl group, i-butylthiocarbonyl group, s-butylthiocarbonyl group or t-butylthiocarbonyl group;

(62) alkylthioalkyl groups such as a methylthiomethyl group or 1-methylthioethyl group; (63) arylthioalkyl groups such as phenylthiomethyl group or 1-phenylthioethyl group; (64) alkylthioalkoxy groups such as a methylthiomethoxy group or 1-methylthioethoxy group; (65) arylthioalkoxy groups such as a phenylthiomethoxy group or 1-phenylthioethoxy group; (66) alkylsulfinyl groups such as a methylsulfinyl group, ethylsulfinyl group or t-butylsulfinyl group; (67) alkenylsulfinyl groups such as an allylsulfinyl group; (68) alkynylsulfinyl groups such as a propargylsulfinyl group; (69) arylsulfinyl groups such as a phenylsulfinyl group; (70) heteroarylsulfinyl groups such as a 2-pyridylsulfinyl group or 3-pyridylsulfinyl group; (71) aralkylsulfinyl groups such as a benzylsulfinyl group or phenethylsulfinyl group; (72) heteroarylalkylsulfinyl groups such as a 2-pyridylmethylsulfinyl group or 3-pyridylmethylsulfinyl group;

(73) alkylsulfonyl groups such as a methylsulfonyl group, ethylsulfonyl group or t-butylsulfonyl group; (74) alkenylsulfonyl groups such as an allylsulfonyl group; (75) alkynylsulfonyl groups such as a propargylsulfonyl group; (76) arylsulfonyl groups such as a phenylsulfonyl group; (77) heteroarylsulfonyl groups such as a 2-pyridylsulfonyl group or 3-pyridylsulfonyl group; (78) aralkylsulfonyl groups such as a benzylsulfonyl group or phenethylsulfonyl group; (79) heteroarylalkylsulfonyl groups such as a 2-pyridylmethylsulfonyl group or 3-pyridylmethylsulfonyl group; (80) unsaturated 5-membered heterocyclic groups such as a furan-2-yl group, furan-3-yl group, thiophen-2-yl group, thiophen-3-yl group, pyrrol-2-yl group, pyrrol-3-yl group, oxazol-2-yl group, oxazol-4-yl group, oxazol-5-yl group, thiazol-2-yl group, thiazol-4-yl group, thiazol-5-yl group, isoxazol-3-yl group, isoxazol-4-yl group, isoxazol-5-yl group, isothiazol-3-yl group, isothioazol-4-yl group, isothiazol-5-yl group, imidazol-2-yl group, imidazol-4-yl group, imidazol-5-yl group, pyrazol-3-yl group, pyrazol-4-yl group, pyrazol-5-yl group, 1,3,4-oxadiazol-2-yl group, 1,3,4-thiadiazol-2-yl group, 1,2,3-triazol-4-yl group, 1,2,4-triazol-3-yl group or 1,2,4-triazol-5-yl group;

(81) unsaturated 6-membered heterocyclic groups such as a pyridin-2-yl group, pyridin-3-yl group, pyridine-4-yl group, 5-chloro-3-pyridyl group, 3-trifluoromethyl-2-pyridyl group, pyridazin-3-yl group, pyridazin-4-yl group, pyrazin-2-yl group, pyrimidin-5-yl group, 1,3,5-triazin-2-yl group or 1,2,4-triazin-3-yl group; (82) saturated or partially unsaturated heterocyclic groups such as a tetrahydrofuran- 2-yl group, tetrahydrofuran-4-yl group, piperidin-3-yl group, pyrrolidin-2-yl group, morpholino group, piperidino group, N-methylpiperazino group or oxazolin-2-yl group; (83) heterocyclooxy groups such as a 2-pyridyloxy group or 3-isoxazolyloxy group; (84) heteroarylalkyl groups such as a 2-pyridylmethyl group or 3-pyridylmethyl group; and, (85) heteroarylalkoxy groups such as a 2-pyridylmethoxy group or 3-pyridylmethoxy group.

These substituents exemplified in (1) to (85) are able to further have the substituents exemplified in (1) to (85) therein within a chemically acceptable range.

Specific examples of substituted aryl groups include a 4-fluorophenyl group, 4-chlorophenyl group, 2,4-dichlorophenyl group, 3,4-dichlorophenyl group, 3,5-dichlorophenyl group, 2,6-difluorophenyl group, 4-trifluoromethylphenyl group, 4-methoxyphenyl group, 3,4-dimethoxyphenyl group, 3,4-methylenedioxyphenyl group, 4-trifluoromethoxyphenyl group, 4-methoxy-1-naphthyl group, 4-ethoxyphenyl group and 4-methylphenyl group.

Among these, the compound represented by general formula (s1) is preferably that in which n is an integer of 0 to 3 and A represents a halogen atom, alkyl group or alkoxy group, more preferably that in which n is an integer of 0 to 3 and A represents a halogen atom, and even more preferably a compound in which n is 0.

The cyanide compound represented by general formula (III) is preferably a compound in which r is 0 or 1, p is 0 or 1, $R^1$ represents a linear alkylene group having 1 to 3 carbon atoms or a branched alkylene group having 3 carbon atoms, q is 1 and $R^2$ is a group represented by general formula (s1), more preferably a compound represented by the following general formulas (III-1) to (111-48), even more preferably a compound represented by the following general formulas (III-1) to (111-32), still more preferably a compound represented by the following general formula (III-1), (III-9), (III-17) or (111-25), and particularly preferably a compound represented by the following general formula (III-1) or (III-9). In general formulas (III-1) to (111-48), $R^{1'}$ represents a linear alkylene group having 1 to 3 carbon atoms or a branched alkylene group having 3 carbon atoms and X represents a halogen atom.

[Chemical Formula 10]

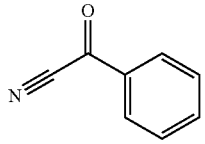
(III-1)

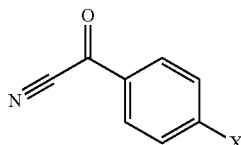
(III-2)

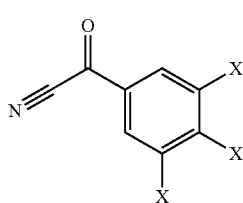
(III-3)

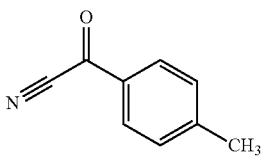
(III-4)

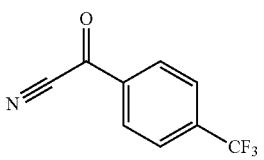
(III-5)

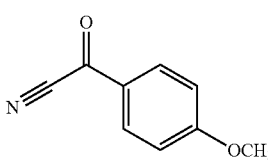
(III-6)

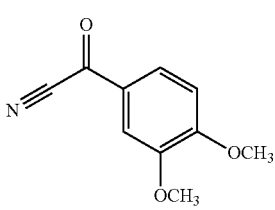
(III-7)

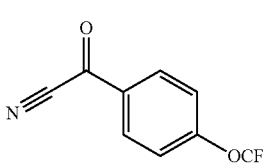
(III-8)

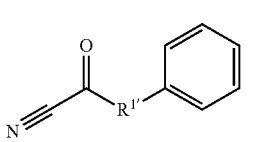
(III-9)

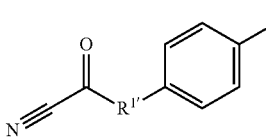
(III-10)

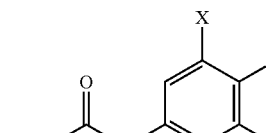
(III-11)

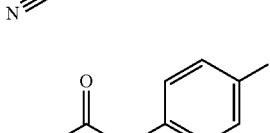
(III-12)

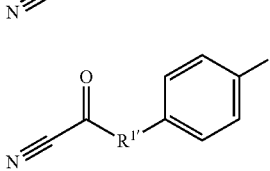
(III-13)

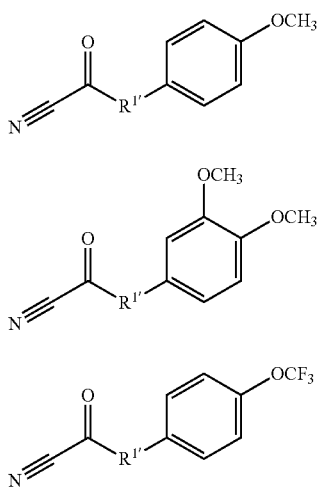
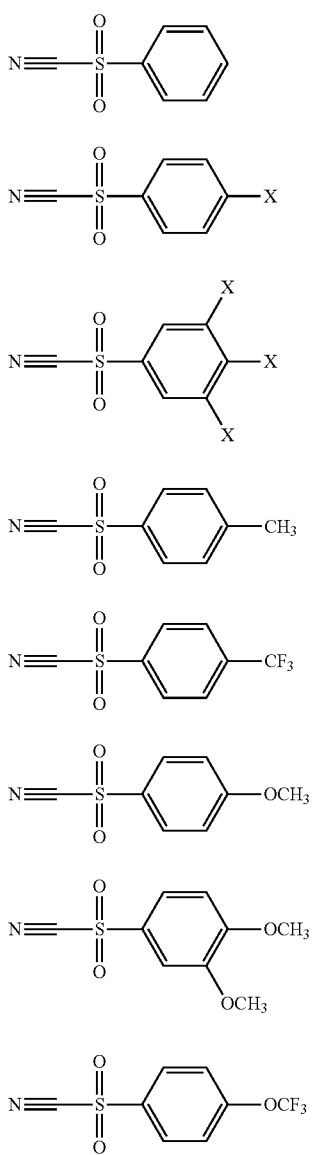
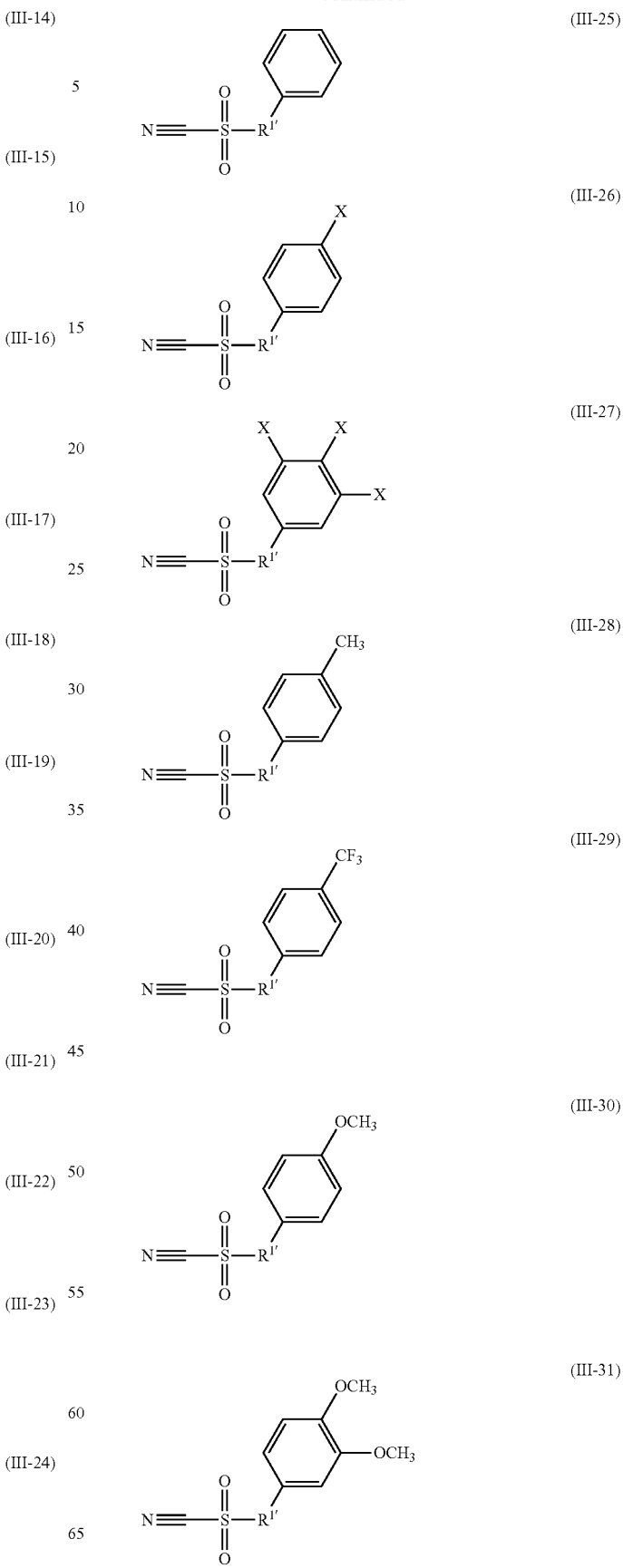

-continued

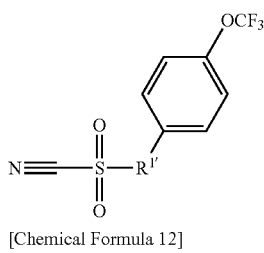

[Chemical Formula 12]

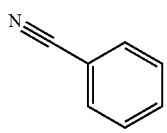

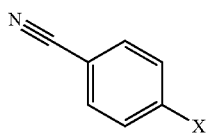

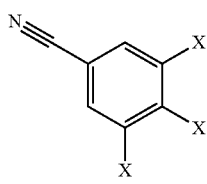

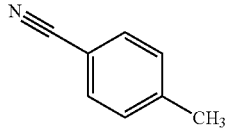

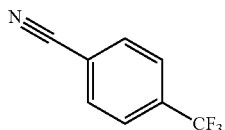

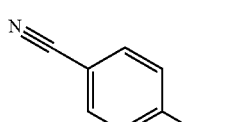

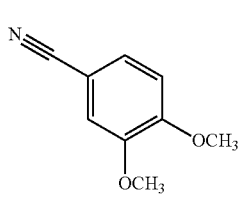

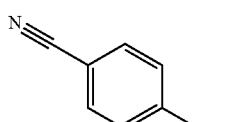

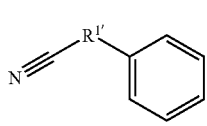

(III-32)

(III-33)

(III-34)

(III-35)

(III-36)

(III-37)

(III-38)

(III-39)

(III-40)

(III-41)

(III-42)

(III-43)

(III-44)

(III-45)

(III-46)

(III-47)

(III-48)

The cyanide compound represented by general formula (III) can be synthesized from a known compound using a known chemical reaction. For example, among cyanide compounds represented by general formula (III), a compound (benzoylcyanide derivative) in which Z represents a carbonyl group, p is 0, q is 1, r is 1 and $R^2$ is a group represented by general formula (s1) can be produced by reacting a benzoyl halide derivative and a cyanide derivative.

[Flow Reactor]

In the production method of the present invention, a flow reactor is used for the reaction vessel used to react the cyanide compound represented by general formula (III) (to also be simply referred to as the "cyanide compound") and the azide compound represented by general formula (II) (to also be simply referred to as the "azide compound"). Consequently, the reaction can be carried out comparatively safely in a high temperature environment even when reacting a highly decomposable compound in the manner of an azide compound.

The flow reactor used in the production method of the present invention is provided with raw material introduction ports, a product discharge port and a flow path communicating there between. Raw materials are supplied through the aforementioned raw material introduction ports and the product obtained by a reaction that occurs in the aforementioned flow path is removed from the aforementioned product discharge port. The aforementioned flow path may also be provided with at least one of an introduction path, mixer portion and reactor portion (retention portion) as necessary. In the case the flow reactor is provided with a mixer portion, the portion of the flow path communicating between the raw material introduction port and the mixer portion is referred to as an introduction path, while in the case a mixer portion is not present, the portion of the flow path that communicates between the raw material introduction port and the reactor portion is referred to as an introduction path. In addition, the raw material introduction port is normally connected to a container filled with raw material. The product discharge portion may also be connected to a container for storing the product as necessary.

The mixer portion is a site that has the function of mixing a plurality of liquids by dispersion, and solutions supplied from the plurality of raw material introduction ports merge in the mixer portion. In addition, the reactor portion is a site where a reaction is carried out for synthesizing a product from the plurality of raw material compounds (the cyanide compound and azide compound in the production method of the present invention). In the case of being provided with both a mixer portion and a reactor portion, the mixer portion is provided on the side of the raw material introduction ports. In the case of preliminarily supplying a reaction solution obtained by mixing all of the raw material compounds from a single raw material introduction port, the mixer portion need not be provided. In addition, the reactor portion need not be provided in the case the time required by the reaction for synthesizing the product is short and the reaction is able to be completed by the time the raw materials pass through the mixer portion.

In the case the flow reactor is provided with a plurality of raw material introduction ports and introduction paths, the aforementioned flow reactor has a configuration in which the upstream side of the flow path thereof is branched corresponding to the number of introduction paths, and is provided with at least one mixer portion. There are no particular limitations on the number of raw material introduction ports and introduction paths, and can be suitably selected corresponding the particular purpose. In the case of having three or more raw material introduction ports and introduction paths, a configuration may be employed in which liquid supplied from all of the introduction ports merges in a single mixer portion, or a configuration may be employed in which the liquid is allowed to merge in a stepwise manner in two or more mixer portions. For example, after merging liquid supplied from two introduction paths in a first mixer portion, the mixture discharged from the aforementioned mixer portion and liquid introduced from the remaining introduction path can be merged in a second mixer portion.

Furthermore, a portion of the raw materials can be preliminarily charged into the flow path of the flow reactor (such as the mixer portion), and the remaining raw materials may be respectively supplied from one or a plurality of raw material introduction ports.

There are no particular limitations on the material of the aforementioned flow reactor, and can be suitably selected corresponding to the type of required performance, such as heat resistance, pressure resistance, solvent resistance or processing ease. Examples of the aforementioned material include stainless steel, titanium, copper, nickel, aluminum, silicon, fluororesins such as Teflon® or perfluoroalkoxy resin (PFA), trifluoroacetoamide (TFAA) and polyether ether ketone resin (PEEK).

In addition, the material may be substantially the same throughout the entire flow path or different materials may be used for the introduction path, mixer portion and reactor portion, respectively.

There are no particular limitations on the cross-sectional shape of the flow path and may be rectangular, including a square or oblong shape, polygonal, including a triangular or pentagonal shape, star-shaped, or circular, including semi-circular or elliptical shape. The cross-sectional shape of the flow path is not required to be constant. Furthermore, "flow path cross-section" refers to the cross-section in a direction perpendicular to the direction of flow of a reaction solution and the like through the flow path, while "cross-sectional area" refers to the area of the aforementioned cross-section.

There are no particular limitations on the cross-sectional area or flow path length of the flow path, and are suitably adjusted in consideration of such factors as viscosity and flow rate of the reaction solution, reaction temperature or reaction time. If the cross-sectional area of the flow path is excessively small, pressure loss may become high thereby making it difficult to supply raw materials and allow the reaction solution to flow. Conversely, if the cross-sectional area is excessively large, heat exchange efficiency decreases and a temperature distribution and the like occur, thereby impairing the characteristics of the flow reactor. The cross-sectional area of the flow path may be substantially the same throughout the entire flow path or the cross-sectional area may be different in the introduction path, mixer portion and reactor portion, respectively. In the case the aforementioned flow reactor has a plurality of introduction paths, the cross-sectional area of each introduction path may be mutually the same or different.

The mixer portion has a function that mixes a plurality of liquids by dispersion and a function that removes the heat of reaction.

There are no particular limitations on the type of mixing used to mix liquids in the mixer portion, and can be suitably selected corresponding to the particular purpose. For example, mixing may be carried out by laminar flow or turbulent flow.

There are no particular limitations on the mixer portion provided it is provided with a mechanism that is capable of mixing a plurality of liquids, and can be suitably selected corresponding to the particular purpose. Examples of the mixer portion include a T-pipe, micromixer and branched pipe. A T-shape or a Y-shape can be used for the shape of the mixer portion in the case the number of introduction ports is two, while a cross-shape, for example, can be used in the case the number of introduction ports is three.

There are no particular limitations on the cross-sectional area of the mixer portion provided it does not impair the effects of the present invention, and can be suitably adjusted in consideration of such factors such as the type of mixing. Since the mixer portion is able to favorably demonstrate each of the functions of mixing a plurality of liquids by dispersion and removing the heat of reaction, in the case the cross-sectional shape is circular, the mixer portion preferably has an inner diameter of about 10 μm to about 5 cm. In addition, although the cross-sectional area of the mixer portion may be the same as other portions such as the introduction paths, it is preferably larger than the introduction paths from the viewpoint of mixing efficiency.

There are no particular limitations on the flow path length of the mixer portion, and can be suitably adjusted in consideration of such factors as the type of mixing, type and amount of liquid supplied from each introduction path, or the presence or absence of a reactor portion. For example, in the case the cross-sectional shape is circular, the inner diameter can be about 10 μm to about 5 cm and the flow path length can be 10 cm to 50 m.

Although the flow path length of the mixer portion is preferably of a sufficient length for mixing liquids introduced from a plurality of introduction paths by dispersion, in the case of providing a separate reactor portion, the flow path length may be shorter. On the other hand, in the case of not providing a separate reactor portion and obtaining a product following completion of the reaction at the point the liquids have passed through the mixer portion, the flow path length of the mixer portion is preferably suitably adjusted in consideration of the optimum reaction time.

The reactor portion is a site for regulating the length of the flow path and precisely controlling the time required to carry out the reaction (controlling residence time). In a flow reactor, reaction time is equivalent to the residence time in a flow path of a reaction liquid obtained by mixing all raw materials. Since the aforementioned residence time is proportional to flow path length, reaction time is adjusted by adjusting flow path length.

The composition such as the cross-sectional area, inner diameter, outer diameter, flow path length, and materials of the flow path of the reactor portion, can be suitably selected corresponding to the desired reaction. For example, there are no particular limitations on the material of the reactor portion, and those materials listed as examples of materials of the aforementioned flow reactor can be used preferably.

The mixer portion, introduction paths and reactor portion are provided with connecting means for mutually connecting each member as necessary. There are no particular limitations on the connection method used by the aforementioned connecting means, and can be suitably selected from among known tube connection methods corresponding to the particular purpose, with examples of connection methods including threading, union jointing, butt welding, socket welding, flange connection, flareless connection, flared connection and mechanical connection.

There are no particular limitations on the members other than the introduction ports, mixer portion and reactor portion, and can be suitably selected corresponding to the particular purpose. Examples of the aforementioned members include pumps used to pump liquid, temperature control means, reaction accelerating means, sensors, pressure regulating valves, and tanks for storing compounds produced.

There are no particular limitations on the aforementioned pumps, and can be suitably selected from among those compatible with industrial use. Among these, pumps that do not generate pulsation during delivery of liquid are preferable, and examples thereof include plunger pumps, gear pumps, rotary pumps and diaphragm pumps.

There are no particular limitations on the aforementioned temperature control means, and can be suitably selected corresponding to the reaction temperature. Examples thereof include constant temperature baths, circulators and heat exchangers.

[Azide Compound and Cyanide Compound Reaction Conditions]

There are no particular limitations on the solvent of the reaction solution within the flow reactor (solution that results after mixing all raw materials) provided it dissolve both the cyanide compound and the azide compound and it does not inhibit the cycloaddition reaction of the azide compound to the cyanido group of the cyanide compound. Examples of the aforementioned solvent include hydrocarbon-based solvents such as pentane, hexane, heptane, benzene, toluene or xylene, nitrile-based solvents such as acetonitrile or propionitrile, ether-based solvents such as diethyl ether, dioxane or tetrahydrofuran, amide-based solvents such as N,N-dimethylformamide, N,N-dimethylacetamide or N-methylpyrrolidone (NMP), sulfoxide-based solvents such as dimethylsulfoxide, water, and mixed solvents thereof. In addition, an acid such as acetic acid may be added to these organic solvents. In the production method of the present invention, a hydrocarbon-based solvent or amide-based solvent is used preferably, while toluene or NMP is used more preferably.

Although there are no particular limitations on the content ratio of the cyanide compound and azide compound in the reaction solution within the flow reactor (solution resulting after mixing all raw materials) provided it allows the target reaction to proceed, an adequate amount of azide compound relative to the cyanide compound is preferably contained in the reaction solution. For example, the content of the azide compound is preferably 1.4 times or more, more preferably 1.8 times or more, even more preferably 2 times or more, still more preferably 3 times or more, and particularly preferably 4 times or more, the number of moles of the cyanide compound.

There are no particular limitations on the reaction temperature of the reaction solution inside the flow reactor (solution resulting after mixing all raw materials) provided it is a temperature that adequately suppresses the risk of decomposition of the azide compound. For example, the reaction is preferably carried out at 150° C. to 250° C. and more preferably carried out at 150° C. to 220° C.

EXAMPLES

Although the following provides a more detailed explanation of the present invention through examples thereof, the present invention is not limited to these examples.

Example 1

<Synthesis of Methyl Azide>

65.01 g (1 mol) of sodium azide and 159.2 g of pure water were added to a 1 L four-mouth flask to prepare a 29% by weight aqueous sodium azide solution. 71.4 g of a 28% by weight aqueous sodium hydroxide solution (50 mol %) were further added to the aforementioned four-mouth flask followed by heating to 80° C. While maintaining the liquid temperature at 80° C., 184.23 g of dimethyl sulfate (146 mol %) and 14.3 g of a 28% by weight aqueous sodium hydroxide solution (10 mol %) were dropped in followed by allowing to further react for 20 minutes at 80° C. Completion of the reaction was confirmed by HPLC. As a result, 48.34 g of methyl azide (yield: 84.7 mol %) were obtained. 32.27 g of toluene were added to 44.32 g of the methyl azide to obtain a toluene solution containing methyl azide at 54.3% by weight.

<Cycloaddition Reaction>

Cycloaddition reactions were carried out under the conditions described in Table 1 using a flow reactor having an inner diameter of 1 mm and flow path length of 34 m and using benzoyl cyanide and the methyl azide obtained above as raw materials. In Table 1, "R—CN (mol %)" indicates the content of benzoyl cyanide in the reaction solution, while "R—N3 (mol %)" indicates the content of methyl azide in the reaction solution. In addition, "concentration (L/mol)" indicates the amount of solvent relative to the number of moles of the charged raw material in the form of the cyanide compound (R—CN).

TABLE 1

|  | Flow rate (mL/min) | Residence time (min) | R—CN (mol %) | R—N3 (mol %) | Solvent | Concentration (L/mol) | Temp. (° C.) | Reaction time (h) |
|---|---|---|---|---|---|---|---|---|
| Reaction 1 | 0.6 | 25 | 100 | 400 | Toluene | 9.0 | 195 | 5 |
| Reaction 2 | 0.3 | 50 | 100 | 400 | Toluene | 9.0 | 195 | 7.5 |
| Reaction 3 | 0.2 | 50 | 100 | 400 | Toluene | 4.0 | 195 | 5 |
| Reaction 4 | 0.2 | 50 | 100 | 400 | Toluene | 1.4 | 195 | 6.5 |
| Reaction 5 | 0.2 | 50 | 100 | 400 | Toluene | 1.3 | 195 | 6 |

The contents of 1-methy-5-benzoyl-1H-tetrazole (target substance) and benzoyl cyanide (raw material) present in the reaction solution recovered from the product discharge port of the flow reactor were measured. The results are shown in Table 2. As a result, 1-methy-5-benzoyl-1H-tetrazole was able to be obtained in a short period of time and at an extremely high yield in all reactions in comparison with the reaction of Comparative Example 1 using an autoclave to be subsequently described.

TABLE 2

|  | Target Substance (mol %) | Raw Material (mol %) |
|---|---|---|
| Reaction 1 | 25.7 | 64.4 |
| Reaction 2 | 33.9 | 18.9 |
| Reaction 3 | 55.6 | 0.3 |
| Reaction 4 | 68.0 | 2.4 |
| Reaction 5 | 68.6 | 0.8 |

Example 2

<Synthesis of Methyl Azide>

65.01 g (1 mol) of sodium azide and 160.3 g of pure water were added to a 1 L four-mouth flask to prepare a 29% by weight aqueous sodium azide solution. 71.2 g of a 28% by weight aqueous sodium hydroxide solution (50 mol %) were further added to the aforementioned four-mouth flask followed by heating to 80° C. While maintaining the liquid temperature at 80° C., 190.18 g of dimethyl sulfate (151 mol %) and 14.67 g of a 28% by weight aqueous sodium hydroxide solution (10 mol %) were dropped in followed by allowing to further react for 20 minutes at 80° C. Completion of the reaction was confirmed by HPLC. As a result, 53.88 g of methyl azide (yield: 94.2 mol %) were obtained. 33.48 g of N-methylpyrrolidone (NMP) were further added to obtain an NMP solution containing methyl azide at 61.7% by weight.

<Cycloaddition Reaction>

Cycloaddition reactions were carried out under the conditions described in Table 3 using a flow reactor having an inner diameter of 1 mm and flow path length of 34 m and using benzoyl cyanide and the methyl azide obtained above as raw materials. In Table 3, "R—CN (mol %)" indicates the content of benzoyl cyanide in the reaction solution, while "R—N3 (mol %)" indicates the content of methyl azide in the reaction solution. In addition, "concentration (L/mol)" indicates the amount of solvent relative to the number of moles of the charged raw material in the form of the cyanide compound (R—CN).

TABLE 3

|  | Flow rate (mL/min) | Residence time (min) | R—CN (mol %) | R—N3 (mol %) | Solvent | Concentration (L/mol) | Temp. (° C.) | Reaction time (h) |
|---|---|---|---|---|---|---|---|---|
| Reaction 6 | 1.0 | 27 | 100 | 200 | NMP | 0.79 | 198 | 1.5 |
| Reaction 7 | 1.0 | 27 | 100 | 200 | NMP | 1.82 | 198 | 2 |
| Reaction 8 | 1.0 | 27 | 100 | 200 | NMP | 0.27 | 198 | 2 |
| Reaction 9 | 1.0 | 27 | 100 | 400 | NMP | 0.66 | 198 | 2 |
| Reaction 10 | 1.0 | 27 | 100 | 140 | NMP | 0.83 | 198 | 2 |

The contents of 1-methy-5-benzoyl-1H-tetrazole (target substance) and benzoyl cyanide (raw material) present in the reaction solution recovered from the product discharge port of the flow reactor were measured. The results are shown in Table 4. As a result, 1-methy-5-benzoyl-1H-tetrazole was able to be obtained in a short period of time and at an extremely high yield in all reactions in comparison with the reaction of Comparative Example 1 using an autoclave to be subsequently described. In particular, 1-methyl-5-benzoyl-1H-tetrazole was able to be obtained at a yield of 50 mol % or more by adding methyl azide to the reaction solution at 200 mol % or more relative to benzoyl cyanide.

TABLE 4

|  | Target Substance (mol %) | Raw Material (mol %) |
|---|---|---|
| Reaction 6 | 59.7 | 0.3 |
| Reaction 7 | 54.5 | 13.5 |
| Reaction 8 | 62.1 | 0 |
| Reaction 9 | 74.1 | 0 |
| Reaction 10 | 12.7 | 0.2 |

Comparative Example 1

A cycloaddition reaction was carried out under the conditions described in Table 5 using an SUS autoclave and using benzoyl cyanide and the methyl azide synthesized in Example 1 as raw materials. In Table 5, "R—CN (mol %)" and "R—N3 (mol %)" are the same as defined in Table 1.

The contents of 1-methy-5-benzoyl-1H-tetrazole and benzoyl cyanide present in the reaction solution following completion of the reaction were measured. The measurement results are shown in Table 5. Although the reaction was allowed to proceed for a long period of time of 35 hours, the yield of 1-methyl-5-benzoyl-1H-tetrazole was only 2.4 mol %.

TABLE 5

|  | R—CN (mol %) | R—N3 (mol %) | Solvent | Concentration (L/mol) | Temp. (° C.) | Reaction time (h) | Target substance (mol %) |
|---|---|---|---|---|---|---|---|
| Reaction 11 | 100 | 400 | Toluene | 0.5 | 80 | 35 | 2.4 |

INDUSTRIAL APPLICABILITY

The present invention is able to provide a method for producing a 1H-tetrazole derivative from an azide compound and a cyanide compound.

According to the production method of the present invention, since a 1H-tetrazole derivative, which has substituents at the 1-position and 5-position and is useful as a synthesis raw material of a tetrazoyl oxime derivative useful as an active ingredient of agricultural chemicals, pharmaceuticals and the like, can be produced efficiently and safely, the production method of the present invention can be used in manufacturing fields such as agricultural chemicals or pharmaceuticals.

The invention claimed is:

1. A method for producing a 1H-tetrazole of formula (I), comprising:

reacting an azide compound represented by the following general formula (II) with a cyanide compound represented by the following general formula (III) in a flow reactor to produce a compound represented by the following general formula (I):

$$Y—N_3 \quad (II)$$

wherein, Y represents an alkyl group, aryl group or arylalkyl group;

(III)

wherein, Z represents —CO— or —SO$_2$—, p represents 0 or 1, q represents 0 or 1, r represents 1, R$^1$ represents an alkyl group or hydrogen atom when q is 0 or an alkylene group or hydrogen atom when q is 1 and R$^2$ represents an unsubstituted or substituted aryl group, provided that q is 1 when p is 0;

[Chemical Formula 3]

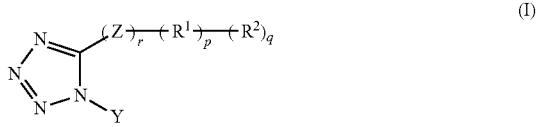
(I)

wherein, Y is the same as defined in general formula (II) and Z, R$^1$, R$^2$, p, q and r are the same as defined in general formula (III), wherein
the reaction temperature is 150° C. to 250° C., and
the solvent in the reaction solution of the reaction is toluene or N-methylpyrrolidone.

2. The method for producing a 1 H-tetrazole of formula (I), according to claim 1, wherein Y represents an alkyl group.

3. The method for producing a 1H-tetrazole of formula (I) according to claim 1, wherein R$^2$ is a group represented by the following general formula (s1):

(s1)

wherein, A represents a halogen atom, alkyl group, haloalkyl group, alkoxy group, haloalkoxy group, alkylsulfonyl group, unsubstituted or substituted aryl group, cyano group or nitro group, n represents an integer of 0 to 5, A may be mutually the same or different when n is 2 or more, and the asterisk (*) represents bonding to R1 when p is 1 in the general formula (III), bonding to Z when p is 0.

4. The method for producing a 1H-tetrazole of formula (I) according to claim 1, wherein the reaction solution of the reaction contains the azide compound represented by general formula (II) in an amount equal to 1.4 times or more the number of moles of the cyanide compound represented by general formula (III).

* * * * *